(12) United States Patent
Facchine et al.

(10) Patent No.: US 12,421,663 B2
(45) Date of Patent: Sep. 23, 2025

(54) SUSPENSIONS INCLUDING CELLULOSE NANOFIBRIL AND POLYESTER

(71) Applicants: North Carolina State University, Raleigh, NC (US); Eastman Chemical Company, Kingsport, TN (US)

(72) Inventors: Emily Facchine, Raleigh, NC (US); Saad A. Khan, Raleigh, NC (US); Orlando Rojas, Vancouver (CA); Richard J. Spontak, Raleigh, NC (US); Soo Ah Jin, Cary, NC (US); Koushik Ghosh, Albuquerque, NM (US)

(73) Assignees: North Carolina State University, Raleigh, NC (US); Eastman Chemical Company, Kingsport, TN (US)

( * ) Notice: Subject to any disclaimer, the term of this patent is extended or adjusted under 35 U.S.C. 154(b) by 709 days.

(21) Appl. No.: 17/609,107

(22) PCT Filed: May 6, 2020

(86) PCT No.: PCT/US2020/031621
§ 371 (c)(1),
(2) Date: Nov. 5, 2021

(87) PCT Pub. No.: WO2020/227372
PCT Pub. Date: Nov. 12, 2020

(65) Prior Publication Data
US 2022/0205183 A1    Jun. 30, 2022

Related U.S. Application Data

(60) Provisional application No. 62/844,273, filed on May 7, 2019.

(51) Int. Cl.
*D21H 11/18*    (2006.01)
*C09D 7/20*    (2018.01)
(Continued)

(52) U.S. Cl.
CPC ............... *D21H 11/18* (2013.01); *C09D 7/20* (2018.01); *C09D 7/70* (2018.01); *C09D 101/02* (2013.01);
(Continued)

(58) Field of Classification Search
CPC ........... C08L 67/00; C08L 1/08; D21H 11/18; C09D 7/20; C09D 7/70; C09D 101/02; C09D 167/00
See application file for complete search history.

(56) References Cited

U.S. PATENT DOCUMENTS

| | | |
|---|---|---|
| 3,018,272 A | 1/1962 | Griffing et al. |
| 3,528,947 A | 9/1970 | Lappin et al. |

(Continued)

FOREIGN PATENT DOCUMENTS

| | | |
|---|---|---|
| CN | 106188633 B | 8/2018 |
| JP | 2012051991 A | 3/2012 |

(Continued)

OTHER PUBLICATIONS

Walls et al., "Yield Stress and Wall Slip Phenomena in Colloidal Silica Gels", J. Rheol., 2003, vol. 47, No. 4, pp. 847-868.
(Continued)

*Primary Examiner* — Arrie L Reuther
*Assistant Examiner* — Olga Lucia Donahue
(74) *Attorney, Agent, or Firm* — Michael Best & Friedrich LLP

(57) ABSTRACT

Suspensions can include a polar solvent, sulfonated polyester material dispersed in the polar solvent, and cellulose nanofibril material dispersed in the polar solvent. Suspensions disclosed and contemplated herein leverage polyester that can be used to independently control film formation and rheology. In some instances, polyesters used in suspensions (Continued)

disclosed herein can perform the role of two additives: aqueous thickener and film reinforcement.

18 Claims, 12 Drawing Sheets

(51) Int. Cl.
    C09D 7/40      (2018.01)
    C09D 101/02    (2006.01)
    C09D 167/00    (2006.01)
    D21H 17/53    (2006.01)
    D21H 23/04    (2006.01)

(52) U.S. Cl.
    CPC .......... *C09D 167/00* (2013.01); *D21H 17/53* (2013.01); *D21H 23/04* (2013.01)

(56) References Cited

U.S. PATENT DOCUMENTS

| | | |
|---|---|---|
| 3,779,993 A | 12/1973 | Kibler et al. |
| 4,304,901 A | 12/1981 | O'Neill et al. |
| RE34,716 E | 9/1994 | Vishnupad et al. |
| 5,369,211 A | 11/1994 | George et al. |
| 6,162,890 A | 12/2000 | George et al. |
| 6,171,685 B1 | 1/2001 | George et al. |
| 6,428,900 B1 | 8/2002 | Wang |
| 7,902,094 B2 | 3/2011 | Haile et al. |
| 7,923,526 B2 | 4/2011 | Oldfield et al. |
| 8,512,519 B2 | 8/2013 | Gupta et al. |
| 8,580,872 B2 | 11/2013 | Kuo et al. |
| 11,278,475 B2 | 3/2022 | Truniger et al. |
| 2005/0044642 A1 | 3/2005 | Butcher |
| 2006/0058438 A1 | 3/2006 | Williams et al. |
| 2007/0258935 A1 | 11/2007 | McEntire et al. |
| 2009/0123767 A1 | 5/2009 | Gohl et al. |
| 2013/0023604 A1 | 1/2013 | Kuo et al. |
| 2014/0357789 A1 | 12/2014 | George et al. |
| 2015/0175820 A1 | 6/2015 | Breton et al. |
| 2015/0265519 A1 | 9/2015 | Bui et al. |
| 2016/0051460 A1 | 2/2016 | Ebanks et al. |
| 2016/0168443 A1 | 6/2016 | Lafitte et al. |
| 2017/0174980 A1 | 6/2017 | Ladva et al. |
| 2019/0008749 A1 | 1/2019 | Harris et al. |
| 2020/0330356 A1 | 10/2020 | Guariloff |

FOREIGN PATENT DOCUMENTS

| | | |
|---|---|---|
| JP | 2017043647 A | 3/2017 |
| JP | 2018070835 A | 5/2018 |
| JP | 2020055898 A | 4/2020 |
| WO | 2006028680 A1 | 3/2006 |
| WO | 2017080734 A1 | 5/2017 |
| WO | 2018012643 A1 | 1/2018 |
| WO | 2018182721 A1 | 10/2018 |

OTHER PUBLICATIONS

Wei et al., "Environmental Science and Engineering Applications of Nanocellulose-Based Nanocomposites", Env. Sci Nano, 2014, vol. 1. No. 4, pp. 302-316.
Xiang et al., "How Cellulose Nanofibrils Affect Bulk, Surface, and Foam Properties of Anionic Surfactant Solutions", Biomacromolecules, 2019, vol. 20, No. 12, pp. 4361-4369.
Xiang et al., "Surface Activity and Foaming Capacity of Aggregates Formed between an Anionic Surfactant and Non-Cellulosics Leached from Wood Fibers", Biomacromolecules, 2019, vol. 20, No. 6, pp. 2286-2294.
Xu et al., "Decoupling Arrest Origins in Hydrogels of Cellulose Nanofibrils", ACS Omega, 2018, vol. 3, pp. 1564-1571.
Yang et al., "Some Rheological Measurements on Magnetic Iron Oxide Suspensions in Silicone Oil", J. Rheol, 1986, vol. 30, No. 5, pp. 1015-1029.
Zhang et al., "Cellulose Nanofibrils: From Strong Materials to Bioactive Surfaces", J. Renew. Mater., 2013, vol. 1, No. 3, pp. 195-211.
European Patent Office Extended European Search Report for application 20801503.2, dated Jan. 4, 2023, 7 pages.
Abd El-Fattah et al., "Nanocrystalline Cellulose as an Eco-Friendly Reinforcing Additive to Polyurethane Coating for Augmented Anticorrosive Behavior", Carbohydr. Polym., 2018, vol. 183, pp. 311-318.
Agoda-Tandjawa et al., "Rheological Characterization of Microfibrillated Cellulose Suspensions after Freezing", Carbohydr. Polym., 2010, vol. 3, No. 80, pp. 677-686.
Arya et al., "Log-Rolling Micelles in Sheared Amphiphillic Thin Films", Phys. Rev. Lett., 2005, vol. 95, No. 18, 188301.
Azzam et a l., "Tunable Aggregation and Gelation of Thermoresponsive Suspensions of Polymer-Grafted Cellulose Nanocrystals", Biomacromolecules, 2016, vol. 17, No. 6, pp. 2112-2119.
Bjorkman, "Floc Dynamics in Flowing Fibre Suspensions", Nord. Pulp Pap. Res. J., 2005, vol. 20, No. 2, pp. 247-252.
Burns et al., "Nanodiamond Gels in Nonpolar Media: Colloidal and Rheological Properties", J. Rheol., 2014, vol. 58, No. 5, pp. 1599-1614.
Cheng et al., "A Time-Dependent Property and How to Measure It", Rheol. Acta, 1986, vol. 25, No. 5, pp. 542-554.
Chinga-Carrasco, "Cellulose fibres, Nanofibrils and Microfibrils: The Morphological Sequence of MFC Components from a Plant Physiology and Fibre Technology Point of View", Nanoscale Res. Lett., 2011, vol. 6, No. 417, pp. 1-7.
Derakhshandeh et al., "Ageing, Yielding, and Rheology of Nanocrystalline Celluose Suspensions", J. Rheol., 2013, vol. 57, No. 1, pp. 131-148.
Derakhshandeh et al., "Rheology of Pulp Fibre Suspensions: A Critical Review", Chem. Eng. Sci., 2011, vol. 66, No. 15, pp. 3460-3470.
Deshmukh et al., "Biopolymer Composites with High Dielectric Performance: Interface Engineering", Biopolymer Composites in Electronics, Chapter 3, 2017, pp. 27-37.
Dimic-Misic et al., "Micro- and Nanofibrillated Cellulose as a Rheology Modifier Additive in CMC-Containing Pigment-Coating Formulations", Ind. Eng. Chem. Res., 2013, vol. 52, No. 45, pp. 16066-16083.
Fall et al., "Yield Stress and Shear Banding in Granular Suspensions", Phys. Rev. Lett., 2009, vol. 103, No. 17, 178301.
Frisoni et al., "Natural Cellulose Fibers: Heterogeneous Acetylation Kinetics and Biodegradation Behavior", Biomacromolecules, 2001, vol. 2, No. 2, pp. 476-482.
Fukuzumi et al., "Transparent and High Gas Barrier Films of Cellulose Nanofibers Prepared by TEMPO-Mediated Oxidation", Biomacromolecules, 2009, vol. 10, pp. 162-165.
Geng et al., "Chapter 6 Rheological Properties of Jute-Based Cellulose Nanofibers under Different Ionic Conditions", ACS, 2017, vol. 1251, pp. 113-132.
Hill et al., "Elastic Modulus of Microfibrillar Cellulose Gels", Biomacromolecules, 2008, vol. 9, pp. 2963-2966.
Hyun et al., "A Review of Nonlinear Oscillatory Shear Tests: Analysis and Application of Large Amplitude Oscillatory Shear (LAOS)", Prog. Polym. Sci., 2011, vol. 36, No. 12, pp. 1697-1753.
Hyun et al., "Large Amplitude Oscillatory Shear as a Way to Classify the Complex Fluids", J. Non-Newton. Fluid Mech., 2002, vol. 107, No. 1, pp. 51-65.
Ilzhoefer et al., "Evidence of Hierarchical Order in an Amphiphillic Graft Terolymer Gel", J. Phys. Chem., 1995, vol. 99, No. 32, pp. 12069-12071.
International Preliminary Report on Patentability for Application No. PCT/US20/31621 dated Nov. 2, 2021 (5 pages).
International Search Report and Written Opinion for Application No. PCT/US20/31621 dated Jul. 31, 2020 (12 pages).
International Search Report and Written Opinion for Application No. PCT/US20/61048 dated Feb. 17, 2021 (12 pages).
Iotti et al., "Rheological Studies of Microfibrillar Cellulose Water Dispersions", J. Polym. Environ., 2011, vol. 19, pp. 137-145.
Isogai et al., "TEMPO-Oxidized Cellulose Nanofibers", Nanoscale, 2011, vol. 3, pp. 71-85.

(56) References Cited

OTHER PUBLICATIONS

Iwamoto et al., "Relationship between Aspect Ratio and Suspension Viscosity of Wood Cellulose Nanofibers", Polym. J., 2014, vol. 46, No. 1, pp. 73-76.
Karppinen et al., "Flocculation of Microfibrillated Cellulose in Shear Flow", Cellulose, 2019, 2012, vol. 19, No. 6, pp. 1807-1819.
Kaur et al., "Dispersion of Nanomaterials in Aqueous Media: Towards Protocol Optimization", J. Vis. Exp, 2017, vol. 130, e56074, 23 pages.
Klemm et al., "Nanocellulose as a Natural Source for Groundbreaking Applications in Materials Science: Today's State", Mater. Tody, 2018, vol. 21, No. 7, pp. 720-748.
Koumakis et al., "Two Step Yielding in Attractive Colloids: Transition from Gels to Attractive Glasses", Soft Matter, 2011, vol. 7, pp. 2456-2470.
Lasseuguette et al., "Rheological Properties of Microfibrillar Suspension of TEMPO-Oxidized Pulp", Cellulose, 2008, vol. 15, No. 3, pp. 425-433.
Le et al., "Effect of Lignin on the Morphology and Rheological Properties of Nanofibrillated Cellulose Produced from gamma-Valerolactone/Water Fractionation Process", Cellulose, 2018, vol. 25, No. 1, pp. 179-194.
Martoia et al., "Micro-Mechanics of Electrostatically Stabilized Suspensions of Cellulose Nanofibrils under Steady State Shear Flow", Soft Matter, 2016, vol. 12, No. 6, pp. 1721-1735.
Martoia et al., "On the Origins of the Elasticity of Cellulose Nanofiber Nanocomposites and Nanopapers: A Micromechanical Approach", RSC Adv., 2016, vol. 6, No. 53, pp. 47258-47271.
Mason et al., "Elasticity of Compressed Emulsions", Phys. Rev. Lett., 1995, vol. 75, No. 10, pp. 2051-5054.
Moghimi et al., "Colloidal Gels Tuned by Oscillatory Shear", Soft Matter, 2017, vol. 13, No. 12, pp. 2371-2383.
Moon et al., "Cellulose Nanomaterials Review: Structure, Properties and Nanocomposites", Chem. Soc. Rev., 2011, vol. 40, No. 7, pp. 3941-3994.
Nazari et al., "Rheology of Cellulose Nanofibers Suspensions: Boundary Driven Flow", J. Rheol. 1978-Present, 2016, vol. 60, No. 6, pp. 1151-1159.
Nechyporchuk et al., "Current Progress in Rheology of Cellulose Nanofibril Suspensions", Biomacromolecules, 2016, vol. 17, No. 7, pp. 2311-2320.
Nechyporchuk et al., "Rheological Properties of Micro-/Nanofibrillated Cellulose Suspensions: Wall-Slip and Shear Banding Phenomena", Carbohydr. Polmy., 2014, vol. 112, pp. 432-439.
Okita et al., "TEMPO-Oxidized Cellulose Nanofibrils Dispersed in Organic Solvents", Biomacromolecules, 2011, vol. 12, No. 2, pp. 518-522.
Paakko et al., "Enzymatic-Hydrolysis Combined with Mechanical Shearing and High-Pressure Homogenization for Nanoscale Cellulose Fibrils and Strong Gels", Biomacromolecules, 2007, vol. 8, No. 6, pp. 1934-1941.
Petekidis et al., "Rearrangements in Hard-Sphere Glasses Under Oscillatory Shear Strain", Phys. Rev. E, 2002, vol. 66, No. 5, 051402.
Puisto et al., "Modeling the Rheology of Nanocelluose Suspensions", Nord. Pulp Pap. Res. J., 2012, vol. 27, No. 2, pp. 277-281.
Raghavan et al., "Shear-induced Microstructural Changes in Flocculated Suspensions of Fumed Silica", J. Rheol., 1995, vol. 39, No. 6, pp. 1311-1325.
Reiner et al., "Chapter 12 Experiences with Scaling-Up Production of TEMPO-Grade Cellulose Nanofibrils", ACS, 2017, vol. 1251, pp. 227-245.
Saarikoski et al., "Flocculated Flow of Microfibrillated Cellulose Water Suspensions: An Imaging Approach for Characterisation of Rheological Behavior", Cellulose, 2012, vol. 19, No. 3, pp. 647-659.
Saarinen et al., "The Effect of Wall Depletion on the Rheology of Microfibrillated Cellulose Water Suspensions by Optical Coherence Tomography", Cellulose, 2014, vol. 21, No. 3, pp. 1261-1275.
Saito et al., "Cellulose Nanofibers Prepared by TEMPO-Mediated Oxidation of Native Cellulose", Biomacromolecules, 2007, vol. 8, No. 8, pp. 2485-2491.
Tao et al., "Brownian Dynamics Simulations of the Self- and Collective Rotational Diffusion Coefficients of Rigid Long Thin Rods", J. Chem. Phys., 2005, vol. 122, No. 24, 244903.
Landry et al. "Nanocrystalline Cellulose: Morphological, Physical and Mechanical Properties" 104-106, 2011.
Peng et al. "Chemistry and Applications of Nanocrystalline Cellulose and Its Derivatives: A Nanotechnology Perspective" 2011 (16 pages).
Eastman AQ water-dispersable film formers. CC-PC-18117. Dated Mar. 2024. (4 pages).

SUSPENSIONS INCLUDING CELLULOSE NANOFIBRIL AND POLYESTER

CROSS-REFERENCE TO RELATED APPLICATIONS

The present application is a national phase filing under 35 U.S.C. § 371 of International Application No. PCT/US2020/031621, filed May 6, 2020, which claims the priority benefit of U.S. Provisional Patent Application No. 62/844,273, filed on May 7, 2019, the entire contents of which are hereby incorporated by reference.

TECHNICAL FIELD

The present disclosure relates to systems and methods for making suspensions. More particularly, systems and methods disclosed and contemplated herein involve suspensions including cellulose nanofibril and polyester.

INTRODUCTION

Additives are used in various industries to selectively improve one or more properties of the resulting product. Water-based products, such as cosmetics, paper, and coatings, can have unique and specific requirements for certain properties, depending upon the usage and end product. Some additives used in water-based products can be directed at changing rheological properties, during the manufacturing process, for the end product, or both. Some additives used in water-based products can be directed at changing strength properties of the end product.

SUMMARY

In one aspect, a suspension is disclosed. The suspension can include a polar solvent, sulfonated polyester material dispersed in the polar solvent, and cellulose nanofibril material dispersed in the polar solvent.

In another aspect, a method for making an aqueous suspension is disclosed. The method can include combining an aqueous sulfonated polyester mixture and an aqueous cellulose nanofibril mixture to form the aqueous suspension.

There is no specific requirement that a material, technique or method relating to suspensions include all of the details characterized herein, in order to obtain some benefit according to the present disclosure. Thus, the specific examples characterized herein are meant to be exemplary applications of the techniques described, and alternatives are possible.

DETAILED DESCRIPTION

Figure 1:
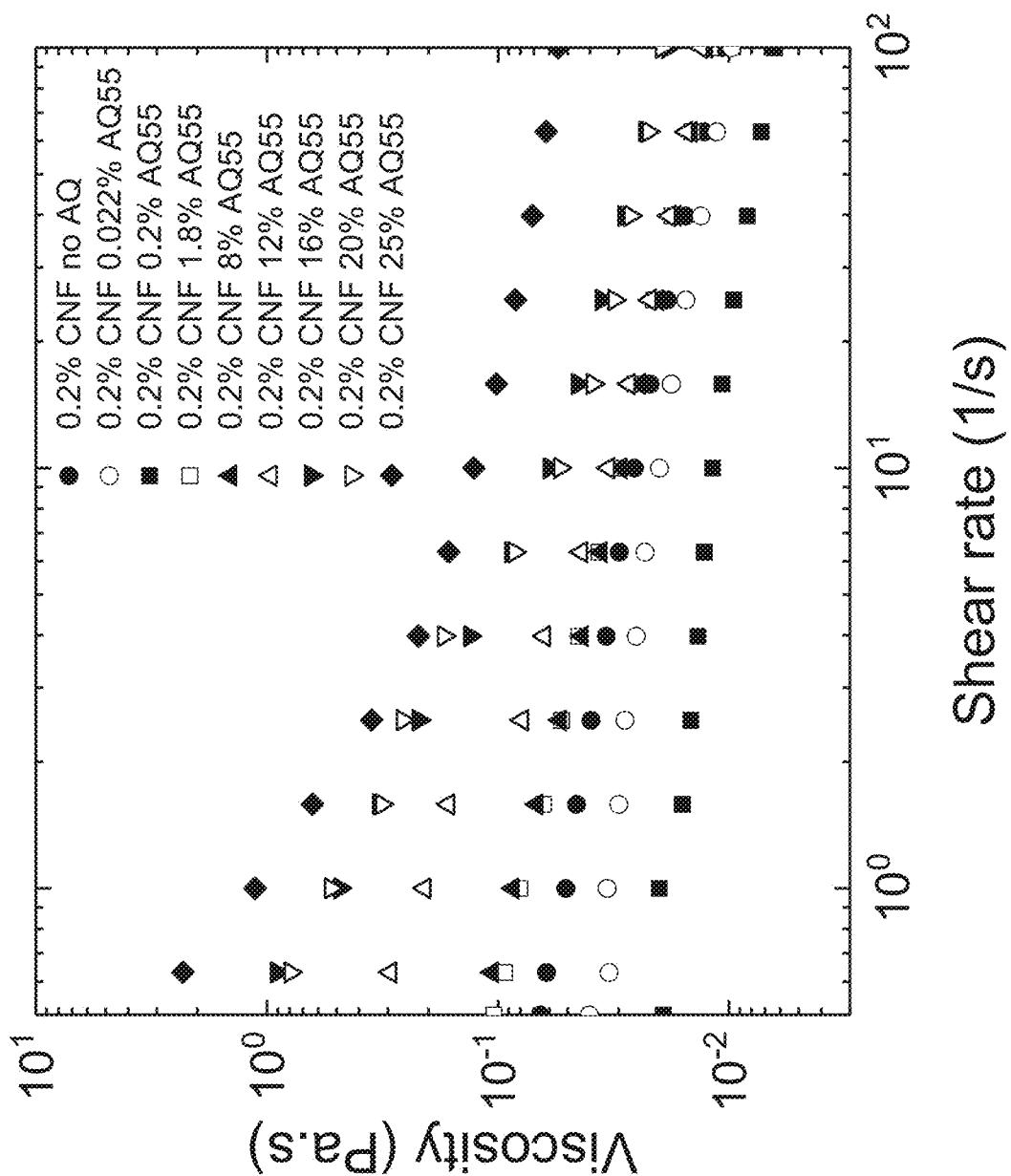
FIG. 1 shows experimental data for viscosity of various example suspensions at selected shear rates, where cellulose nanofibril content was held constant and polyester content was varied.

Systems and methods disclosed and contemplated herein relate to formulations where film formation and rheology can be independently tuned. In some instances, film formation and rheological properties of suspensions can be independently and precisely adjusted on the basis of selective amounts of cellulose nanofibril and polyester. Generally, cellulose nanofibril content in the suspension impacts rheological properties of the suspension, and polyester content in the suspension provides film-forming properties.

Suspensions disclosed and contemplated herein leverage polyester that can be used to independently control film formation and rheology. In some instances, polyesters used in suspensions disclosed herein can perform the role of two additives: aqueous thickener and film reinforcement. In contrast to many existing additives, cellulose nanofibril has relatively low environmental impacts.

A. Definitions

Unless otherwise defined, all technical and scientific terms used herein have the same meaning as commonly understood by one of ordinary skill in the art. In case of conflict, the present document, including definitions, will control. Example methods and materials are described below, although methods and materials similar or equivalent to those described herein can be used in practice or testing of the present disclosure. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein.

For the recitation of numeric ranges herein, each intervening value there between is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated, as are all intermediate values.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

II. Example Suspensions

Example suspensions disclosed and contemplated herein typically include a polar medium, polyester, and cellulose nanofibril. In various implementations, example suspensions can include additional components. The sections below discuss various aspects of exemplary suspensions.

A. Example Polar Media

One or more components of exemplary suspensions are dispersed in a polar medium. In some instances, the polar medium is organic. Typically, exemplary polar media have a dielectric constant (also referred to as "relative permittivity") of from about 24-100. Example polar media include water and ethylene glycol, as well as chemical/physical derivatives and combinations thereof. In some instances, other hydrophilic organic solvents such as glycerol may be used as a polar medium.

B. Example Polyesters

Polyester used in exemplary suspensions provide film-forming properties to the suspensions. As used herein, the term "polyester" means a polymer that encompasses both "homopolyesters" and "copolyesters."

Exemplary polyesters disperse in polar media such as water. Typically, example polyesters disperse without the use of surfactants or other additives. Example polyesters can also aid in the dispersion of hydrophobic constituents in polar media. Example polyesters have glass transition temperature, $T_g$, values of from 35° C. to 55° C.

Typically, polyesters used in exemplary suspensions are sulfonated polyesters. As used herein, the terms "sulfopolyester" and "sulfonated polyester" generally refer to polyesters containing ionic sulfonate ($SO_3^-$) groups, particularly to those synthesized from a sulfomonomer.

Example sulfomonomers include, for instance, 5-sodio-sulfoisophthalic acid (5-SSIPA or SIP) or dimethyl 5-sodio-sulfoisophthalate, as one of the diacids in the polyester compositions. Sulfopolyesters are linear, amorphous polyesters that can be dispersed in water without the assistance of surfactants or amines. This water dispersibility is attributed to the ionic nature of the sulfonate substituents attached to the polymer chains. Examples of commercially-available sulfonated polyesters include Eastman AQ™ 55S polymer, Eastman AQ™ 38S polymer, and Eastman AQ™ 48 polymer. Other sulfonated polyesters are contemplated.

Eastman AQ™ 55S polymer has, on average, a glass transition temperature of 51-55° C., inherent viscosity of 0.29-0.37 dL/g, melt viscosity at 200° C. of 42,000 poise, acid number less than 2 mg KOH/g, hydroxyl number less than 10 mg KOH/g, and bulk density of 0.81 g/cm$^3$ at 23° C.

Eastman AQ™ 38S polymer has, on average, a glass transition temperature of 35-38° C., inherent viscosity of 0.32-0.40 dL/g, melt viscosity at 200° C. of 9,700 poise, acid number less than 2 mg KOH/g, hydroxyl number less than 10 mg KOH/g, and bulk density of 0.78 g/cm$^3$ at 23° C.

Eastman AQ™ 48 Ultra polymer has, on average, a glass transition temperature of 45-48° C., inherent viscosity of 0.26-0.32 dL/g, acid number less than 2 mg KOH/g, hydroxyl number less than 10 mg KOH/g, and bulk density of 0.83 g/cm$^3$ at 23° C.

Additional sulfonated polyesters are disclosed and described in the following documents, each of which is hereby incorporated by reference in their entirety: U.S. Pat. No. 8,580,872, "Sulfopolyester polymer compositions with improved water dispersibility"; United States Pre-Grant Publication No. 2014/0357789, "Sulfopolyester having a charge density greater than one and products made therefrom"; U.S. Pat. No. 7,923,526, "Sulfopolyesters having improved clarity in water-dispersible formulations and products made therefrom"; U.S. Pat. No. 5,369,211, "Water-dispersible sulfopolyester compostions having a TG of greater than 89° C."; U.S. Pat. No. 6,171,685, "Water-dispersible films and fibers based on sulfopolyesters"; U.S. Pat. No. 7,902,094, "Water-dispersible and multicomponent fibers from sulfopolyesters"; and U.S. Pat. No. 6,162,890, "Water-dispersible block copolyesters useful as low-odor adhesive raw materials".

C. Example Cellulose Nanofibril

Example suspensions disclosed and contemplated herein include cellulose nanofibril. Cellulose nanofibril is alternatively referred to as nanofibrillated cellulose or CNF. Cellulose nanofibril is distinguished from crystalline cellulose, such as cellulose nanocrystals (CNC).

Cellulose nanofibril in exemplary suspensions can provide rheological control in the suspension phase. Rheological control can be attributed to the thickening action caused by entanglement and hydrogen bonding of cellulose nanofibril components. Cellulose nanofibril in exemplary suspensions can also provide improved toughness in a dried film. In addition, cellulose nanofibril can have significantly less environmental impact than conventional, synthetic additives, some of which may be petroleum-based.

Cellulose nanofibril can be obtained using methods known in the art, such as by mechanically and/or chemically treating a cellulose suspension. Cellulose suspensions can be prepared from various sources, such as wood, cotton, flax, hemp, bamboo, fungi, algae, rami, sisal, straw, palm, sugar beet pulp, and industrial and crop wastes.

Generally, cellulose nanofibril include fibers having a high aspect ratio (length to width). Cellulose nanofiber width is typically 5 nm to 20 nm. Cellulose nanofibril fibers can have varying lengths, such as 100 nm to 1000 nm. Cellulose nanofibril structure is cellulose I or cellulose 11.

The surface of the cellulose nanofibril may be chemically modified (such as, acetylated, carboxylated, silanised, or modified by other functional groups) whereas the interior of the cellulose nanofibril is cellulose I or cellulose II.

In some instances, cellulose nanofibril used in exemplary suspensions are carboxylated. As used herein, "carboxylated cellulose nanofibril" means cellulose nanofibril fibers include at least one carboxylic acid group. Carboxylated cellulose nanofibril can be obtained using methods known in the art.

D. Example Amounts of Suspension Components

Components in exemplary suspensions disclosed and contemplated herein may be present in various amounts. For instance, sulfonated polyester material can be present in example suspensions at from about 1.8 wt % to about 25.0 wt %. In various implementations, sulfonated polyester material can be present at from 0.18 wt % to 25.0 wt %; from about 0.2 wt % to about 24.0 wt %; from about 2.0 wt % to about 20.0 wt %; from about 5.0 wt % to about 15.0 wt %; from about 8.0 wt % to about 12.0 wt %; from about 1.0 wt % to about 10.0 wt %; from about 10.0 wt % to about 25.0 wt %; from about 15.0 wt % to about 24.0 wt %; from about 3.0 wt % to about 9.0 wt %; from about 20.0 wt % to about 25.0 wt %; or from about 0.3 wt % to about 5.0%. In various implementations, sulfonated polyester material can be present in an amount that is no less than 1.8 wt %; no less than 4 wt %; no less than 8 wt %; no less than 12 wt %; no less than 16 wt %; no less than 20 wt %; or no less than 24 wt %. In various implementations, sulfonated polyester material can be present in an amount no more than 25 wt %; no more than 21 wt %; no more than 17 wt %; no more than 13 wt %; no more than 9 wt %; no more than 5 wt %; or no more than 2 wt %.

Cellulose nanofibril can be present in example suspensions at from about 0.2 wt % to about 10 wt %. In various implementations, cellulose nanofibril can be present at from 0.2 wt % to 10.0 wt %; from about 1.0 wt % to about 9.0 wt %; from about 2.0 wt % to about 8.0 wt %; from about 3.0 wt % to about 7.0 wt %; from about 4.0 wt % to about 6.0 wt %; from about 0.2 wt % to about 5.0 wt %; from about 5.0 wt % to about 10.0 wt %; from about 0.5 wt % to about 3.0 wt %; from about 3.0 wt % to 6.0 wt %; from about 6.0 wt % to about 9.0 wt %; from about 8.0 wt % to about 10.0 wt %; or from about 1.0 wt % to about 4 wt %. In various implementations, cellulose nanofibril can be present in an amount that is no less than 0.2 wt %; no less than 2 wt %; no less than 4 wt %; no less than 6 wt %; no less than 8 wt %; or no less than 9 wt %. In various implementations, cellulose nanofibril can be present in an amount that is no more than 10 wt %; no more than 8 wt %; no more than 6 wt %; no more than 4 wt %; no more than 2 wt %; or no more than 1 wt %.

E. Example Properties

Example suspensions disclosed and contemplated herein have various ranges of physical properties. In accord with standard practice, exemplary values below are obtained as averages of multiple measurements. Techniques described herein can be used to selectively adjust those physical properties depending upon a use or application of the suspension.

Example suspensions can be stable for a given period of time. For instance, example suspensions disclosed and contemplated herein can be stable for about 24 hours to about 1 month, or even longer than 1 month. In some instances, example suspensions can be stable for at least 24 hours; at least 2 days; at least 3 days; at least 7 days; at least 14 days; at least 21 days; at least 28 days; or at least 31 days.

Example suspensions also have various ranges of physical properties after drying, where the resulting product after drying is referred to herein as "dried polymer film." Drying times for exemplary physical properties can be, for instance, about 3 days to about 7 days. In some instances, physical properties described below can be observed after drying for shorter or longer periods of time than about 3 days to about 7 days. Exemplary drying temperatures can be between about 35° C. and about 60° C.

In some instances, dried polymer films can have a Young's Modulus of at least about 1000 MPa but typically not greater than about 2500 MPa. In various implementations, dried polymer film has a Young's Modulus of 1250 MPa to 2250 MPa; of 1500 MPa to 2000 MPa; of from 1750 MPa to 2250 MPa; of from 1250 MPa to 1750 MPa; of from 1000 MPa to 1750 MPa; or of from 2000 MPa to 2500 MPa.

In some instances, dried polymer films have a tensile strength of from about 10 MPa to about 30 MPa. In various implementations, dried polymer films can have a tensile strength of from 10 MPa to 30 Mpa; from 15 MPa to 25 MPa; from 10 MPa to 20 MPa; from 20 MPa to 27 MPa; or from 18 MPa to 25 MPa.

In some instances, dried polymer films have a toughness of from about 0.1 MPa to about 0.25 MPa. In various implementations, dried polymer films can have a toughness of from 0.1 MPa to 0.25 MPa; from 0.15 MPa to 0.25 MPa; from 0.2 MPa to 0.25 MPa; from 0.15 MPa to 0.2 MPa; or from 0.18 MPa to 0.225 MPa.

III. Example Methods of Manufacture

An example method for making suspensions disclosed and contemplated herein can include one or more steps. In some instances, the example method can include preparing a sulfonated polyester mixture. In some instances, the example method can include preparing a cellulose nanofibril mixture.

After preparing or receiving prepared mixtures, the sulfonated polyester mixture is combined with the cellulose nanofibril mixture. In some instances, one or both mixtures are aqueous. In some instances, the mixtures are added to a polar solvent, such as water or ethylene glycol.

Amounts of aqueous sulfonated polyester mixture and aqueous cellulose nanofibril mixture can be determined such that sulfonated polyester material is present in the suspension at no less than 1.8 wt % and no more than 25 wt %, and cellulose nanofibril is present in the suspension at no less than 0.2 wt % and no more than 10 wt %. Other possible amounts of sulfonated polyester material and cellulose nanofibril in the suspension are provided above.

Typically, the combination of mixtures is then mixed using one or more agitation devices. Example agitation devices include probe sonication devices and other devices suited for mixing nanofiber material. In some instances, mixing the combination of sulfonated polyester and cellulose nanofibril occurs in an ice bath.

Mixing of the combined aqueous sulfonated polyester mixture and aqueous cellulose nanofibril mixture can occur for a predetermined amount of time, based on observed or measured properties of the mixture, or other factors. For example, mixing can occur for at least 1 minute; for at least 3 minutes; for at least 5 minutes; for at least 10 minutes; for at least 20 minutes; for at least 30 minutes; for at least 60 minutes; for at least 90 minutes; for at least 120 minutes; for at least 4 hours; for at least 8 hours; for at least 12 hours; for at least 16 hours; for at least 24 hours; for at least 36 hours; or for at least 48 hours.

Mixing can be implemented as sequences where agitation is applied and where agitation is stopped. For example, mixing can include alternating application of energy for a first predetermined amount of time followed by no application of energy for a second predetermined amount of time. In some instances, the first predetermined amount of time is the same as the second predetermined amount of time. In various implementations, the first predetermined amount of time can be at least 1 second; at least 2 seconds; at least 3 seconds; at least 6 seconds; at least 10 seconds; at least 15 seconds; at least 20 seconds; at least 30 seconds; at least 60 seconds; at least 120 seconds; at least 4 minutes; at least 10 minutes; at least 20 minutes; at least 30 minutes; or at least 60 minutes. In some instances, the second predetermined amount of time is the same as the second predetermined amount of time. In various implementations, the first predetermined amount of time can be 1 second; 2 seconds; 3 seconds; 6 seconds; 10 seconds; 15 seconds; 20 seconds; 30 seconds; 60 seconds; 120 seconds; 4 minutes; 10 minutes; 20 minutes; 30 minutes; or 60 minutes. The first predetermined amount of time can be more than, equal to, or less than the second predetermined amount of time.

When a sonicating device is used during mixing, various amplitudes are possible. For example, during mixing, a sonicating device can have an amplitude of about 20%; of about 25%; of about 30%; of about 35%; of about 40%; of about 50%; of about 60%; or of about 70%. Typically, the amplitude of a sonicating device is selected so that none of the components in the aqueous suspension is mechanically or thermally damaged (i.e., adversely altered from their original condition).

In some instances, the aqueous suspension is subjected to a drying process, thereby generating a dried polymer film. A drying process occurs at a drying temperature that is anywhere from slightly below a glass transition temperature to slightly above the glass transition temperature of the sulfonated polyester. For example, a drying temperature can be between about 35° C. and about 60° C. In various implementations, a drying temperature is from 35° C. to 60° C.; from 40° C. to 55° C.; from 45° C. to 50° C.; from 35° C. to 50° C.; from 50° C. to 60° C.; or from 38° C. to 55° C. In various implementations, a drying temperature is no less than 35° C.; no less than 40° C.; no less than 45° C.; no less than 50° C.; or no less than 55° C. In various implementations, a drying temperature is no greater than 60° C.; no greater than 55° C.; no greater than 50° C.; no greater than 45° C.; or no greater than 40° C.

VII. Example Use Implementations

Typically, after preparing the aqueous suspension including sulfonated polyester and cellulose nanofibril, the aqueous suspension can be used as an additive. For instance, the aqueous suspension can be added to a water-based product and/or to a process for making a water-based product. Example products can include coatings, personal care, cosmetics, and paper-based products.

Increased film toughness can improve performance in a number of applications, for example, tear resistance in paper products, durability in coatings, and length of wear in cosmetics. Increase in film flexibility can allow easier handling of the films, because some of pristine AQ films are highly brittle and thus easy to break (difficult to handle the film).

VII. Experimental Examples

Experimental examples were conducted and the results are discussed below.

A. Viscosity Experiments

In a set of experiments, various mixtures were prepared and tested to ascertain and quantify impacts of polyester content on the viscosity of a suspension, holding cellulose nanofibril content constant. Additionally, test samples were prepared to compare the effect of polyester content with that of a conventional polymer, polyvinyl alcohol (PVA).

Each prepared mixture included 0.2 wt % cellulose nanofibril and polymer content was varied. TEMPO-oxidized cellulose nanofibril was purchased from University of Maine as a 1.1% aqueous suspension in neutral form (sodium counterions associated with the carboxyl groups). Fibers produced via this method are known to have diameters on the order of 10 nm and lengths ranging from about 100 nm to about 500 nm. Test mixtures 1-9 used Eastman AQ™ 55 to provide polyester content. Test mixtures 10-12 used polyvinyl alcohol in place of polyester. Components of the aqueous test mixtures are provided below in Table 1.

TABLE 1

Test mixtures for first set of viscosity experiments

| Test Mixture | Cellulose Nanofibril (wt %) | Polyester (wt %) | PVA (wt %) |
|---|---|---|---|
| 1 | 0.2 | 0 | 0 |
| 2 | 0.2 | 0.022 | 0 |
| 3 | 0.2 | 0.2 | 0 |
| 4 | 0.2 | 1.8 | 0 |
| 5 | 0.2 | 8 | 0 |
| 6 | 0.2 | 12 | 0 |
| 7 | 0.2 | 16 | 0 |
| 8 | 0.2 | 20 | 0 |
| 9 | 0.2 | 25 | 0 |
| 10 | 0.2 | 0 | 0.3 |
| 11 | 0.2 | 0 | 1.8 |
| 12 | 0.2 | 0 | 8 |

A stock dispersion of AQ™ 55 was prepared at 30% w/w in water by heating to 65° C. and stirring for 24 hours. PVA stock dispersion was prepared at 10% w/w in water by heating to 80° C. and stirring. Cellulose nanofibril was purchased at 12.1% w/w in water. To prepare test mixtures 1-12, calculated amounts of each suspension were combined with an appropriate amount of deionized water to obtain the desired concentrations. Each mixture was then subjected to probe sonication with a Cole-Parmer 750-Watt Ultrasonic Processor, where the level of sonication was chosen according to the mass of fibrils (2000 J/g CNF). The sonicator was set to 35% amplitude, with a pulsing application of energy 2 seconds on, 3 seconds off, until the desired energy level was reached.

Each test mixture was tested at room temperature and ambient condition. Rheological data were obtained using a rotational rheometer (Discovery Series Hybrid Rheometer (DHR)-3 from TA Instruments, New Castle, Delaware). The rheometer was fixed with a parallel plate test geometry (aluminum plates with 40 mm diameter), and the gap was set to 1000 μm. A sample size of 1.26 mL was used for each test mixture.

Figure 2:
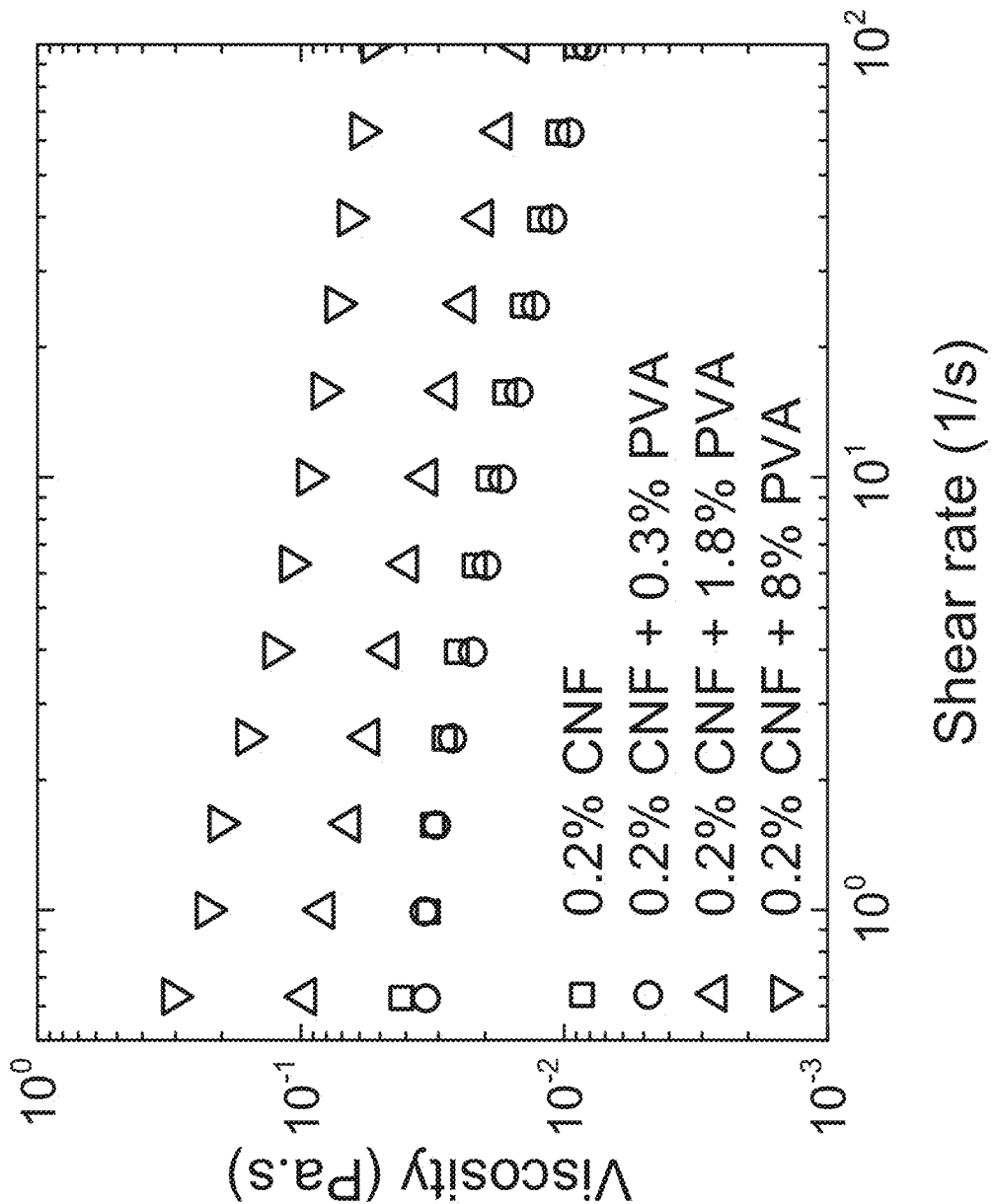
FIG. 2 shows experimental data for viscosity of suspensions with various amounts of polyvinyl alcohol at selected shear rates.

Rheological data for test mixtures 1-9 are shown in FIG. 1. Rheological data for test mixtures 10-12 are shown in FIG. 2. As shown in FIG. 1, small amounts of polyester (up to 0.2 wt %) slightly reduce the viscosity compared to the solution without polyester (test mixture #1). Without being bound by a particular theory, it is hypothesized that the reason for this observed behavior is a combination of screened electrostatic interactions and a potential plasticizing-type mechanism, because the polymer nanoparticles facilitate alignment of the high aspect ratio cellulose nanofibril fibrils under shear.

Observed viscosity of the test mixtures begins to increase above polymer concentrations of 0.2 wt %. At polymer loading around 2-8 wt %, the observed viscosity of the text mixtures approximates that of the test mixture without polymer. At the highest tested polymer concentration, 25 wt %, the observed viscosity is roughly 10 times greater than the test mixture without polymer.

For the PVA-containing mixtures shown in FIG. 2, the viscosity of the mixture with 8 wt % PVA has a roughly 10 times greater viscosity than the test mixture without PVA. That is, the PVA-containing mixtures show the same viscosity increase at smaller polymer loading than the mixtures with polyester.

Figure 3:
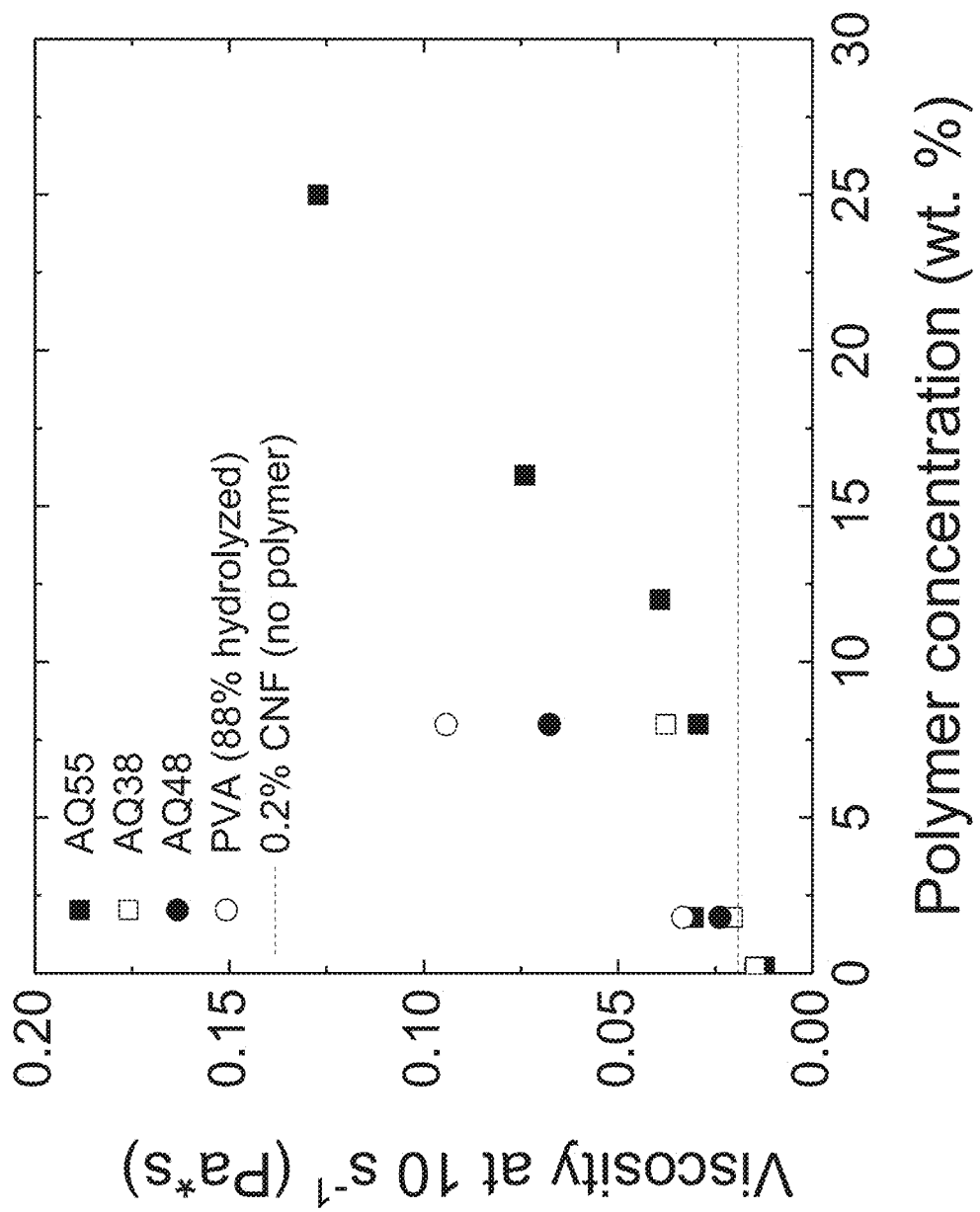
FIG. 3 shows experimental data for viscosity at 10 s' for suspensions with different polymers at different polymer concentrations.
Figure 4:
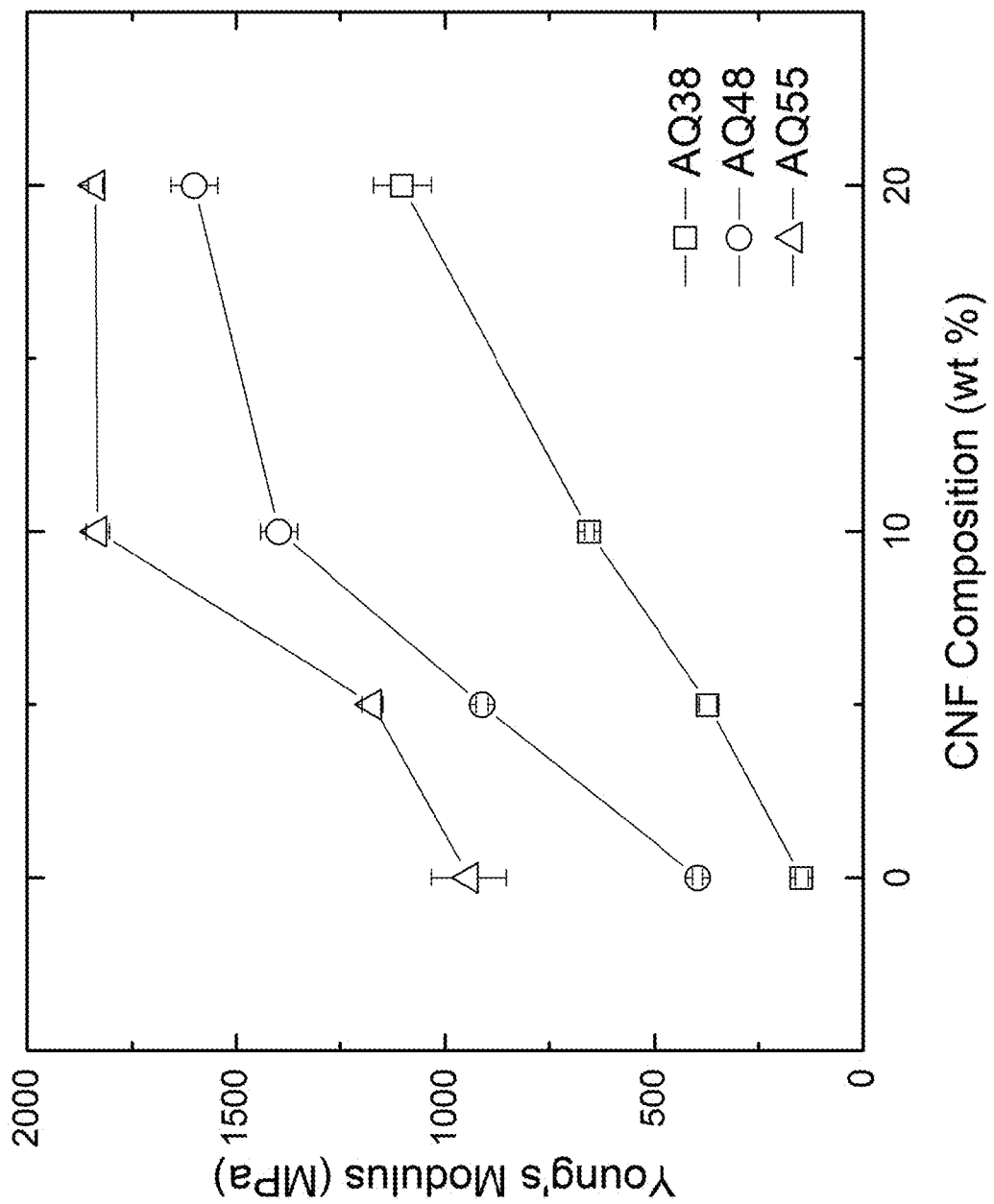
FIG. 4 shows experimental data for Young's Modulus for dried films made from suspensions having different polymers at different polymer concentrations.
Figure 5:
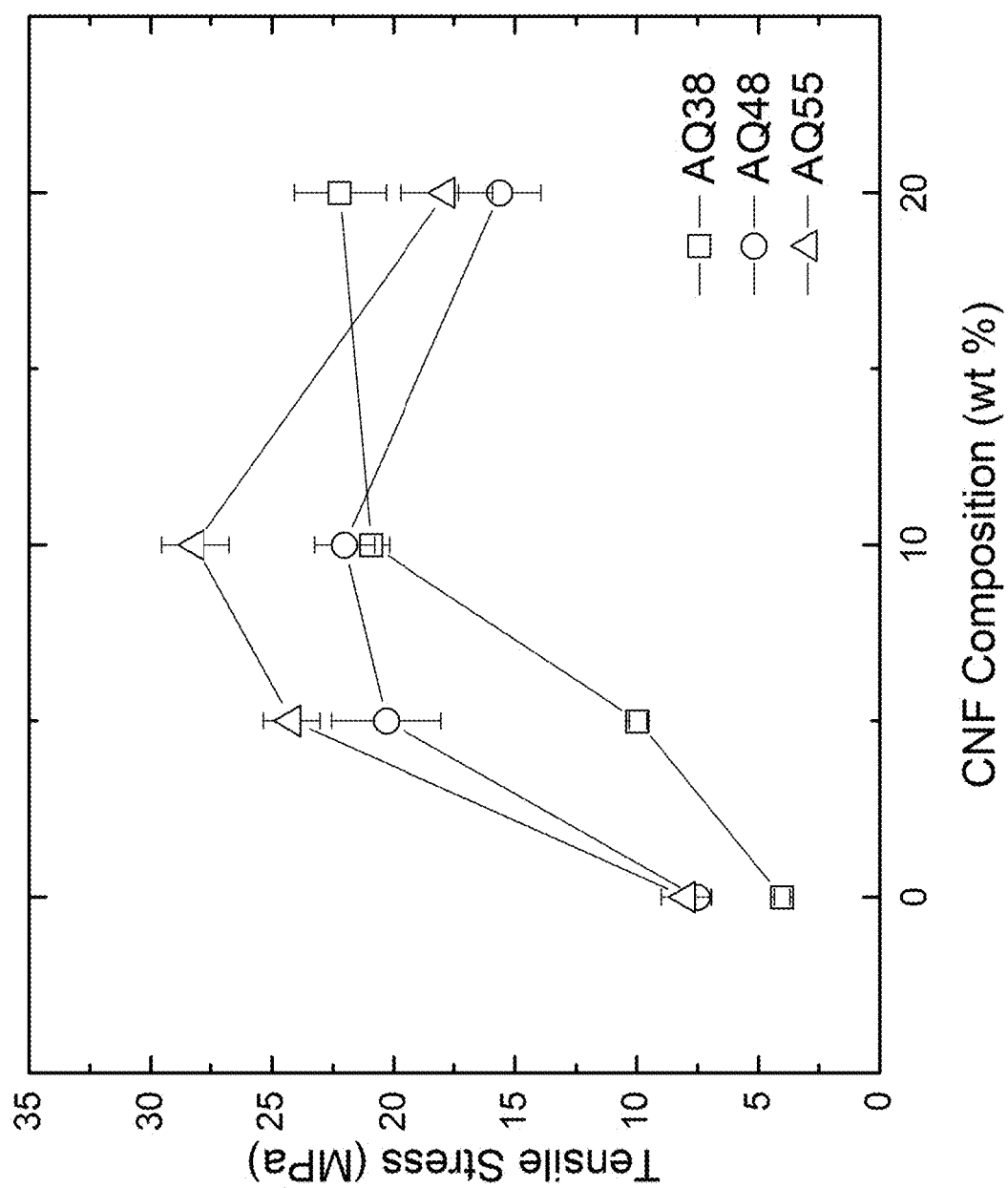
FIG. 5 shows experimental data for Tensile Stress for dried films made from suspensions having different polymers at different polymer concentrations.
Figure 6:
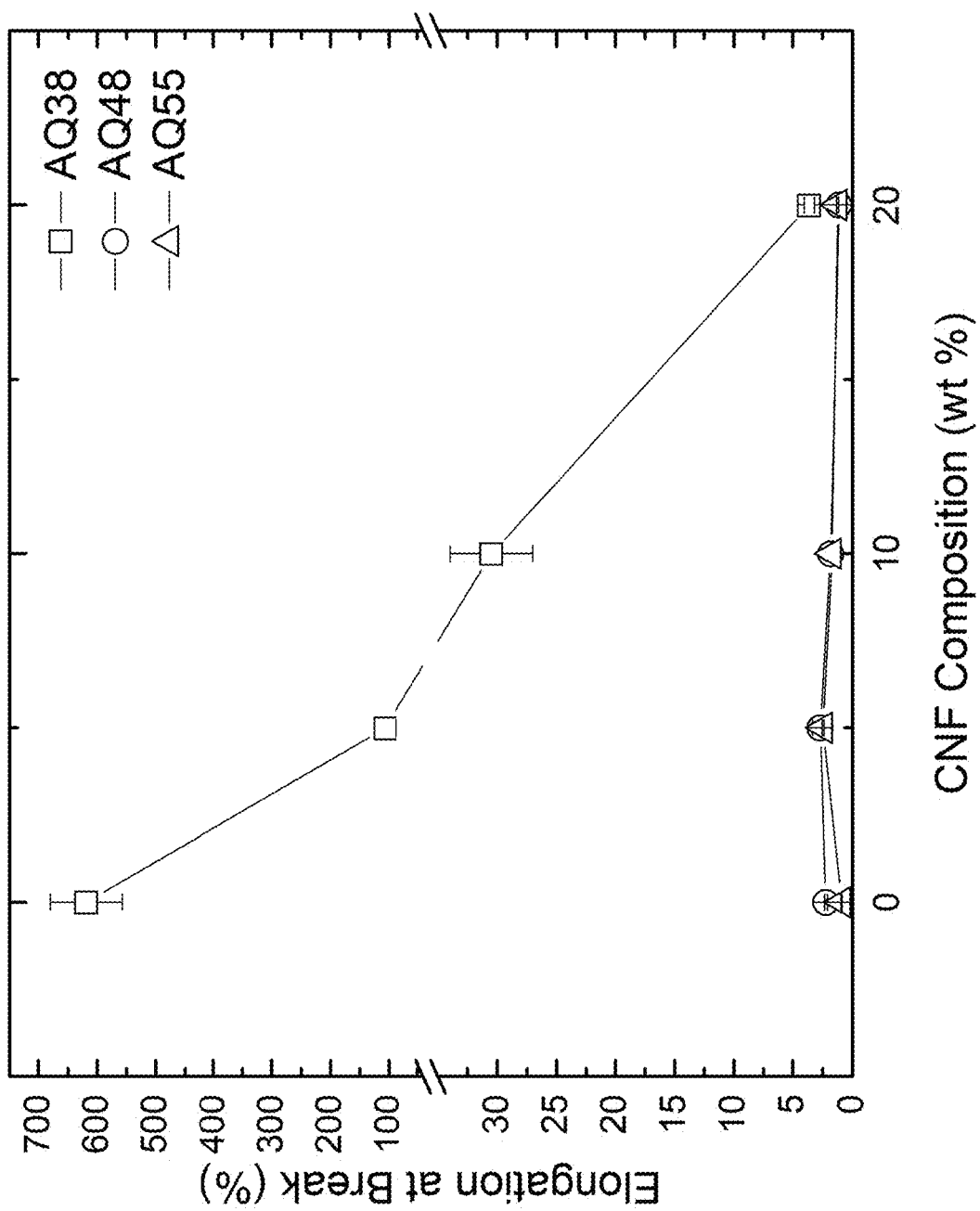
FIG. 6 shows experimental data for Elongation at Break for dried films made from suspensions having different polymers at different polymer concentrations.
Figure 7:
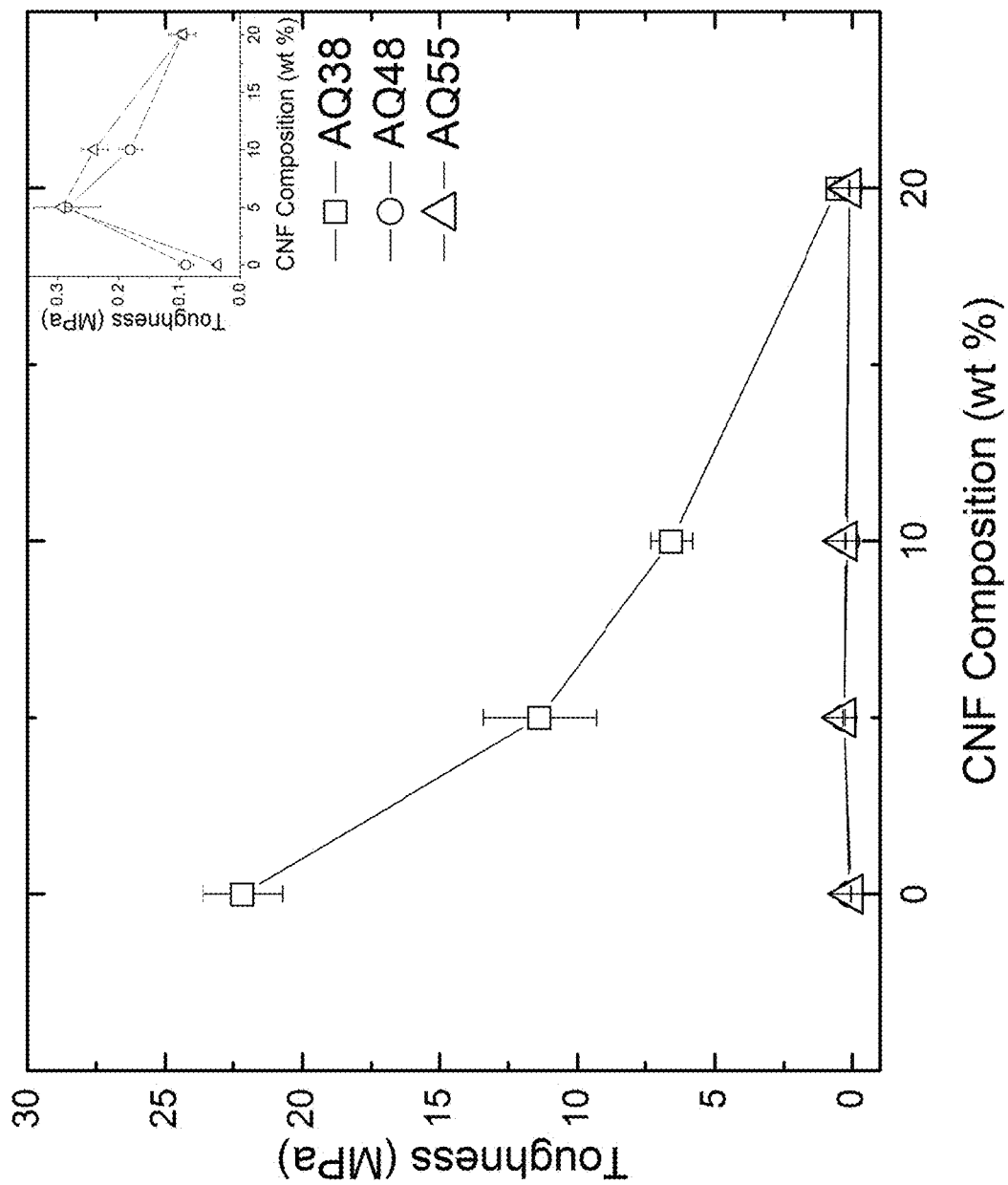
FIG. 7 shows experimental data for Toughness for dried films made from suspensions having different polymers at different polymer concentrations.
Figure 8:
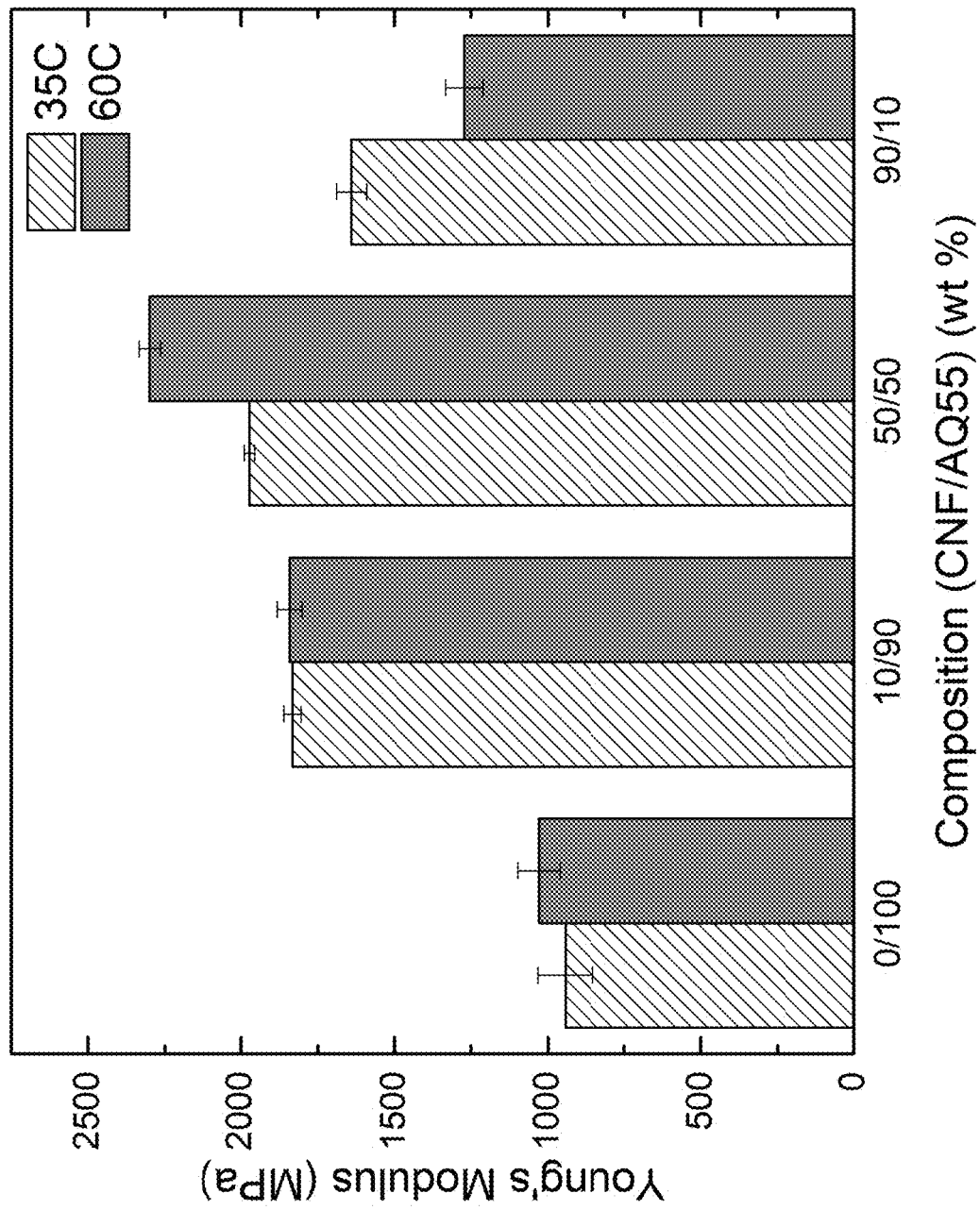
FIG. 8 shows experimental data for Young's Modulus for dried films made from suspensions having different polymer concentrations, where the films were dried at either 35° C. or 60° C.
Figure 9:
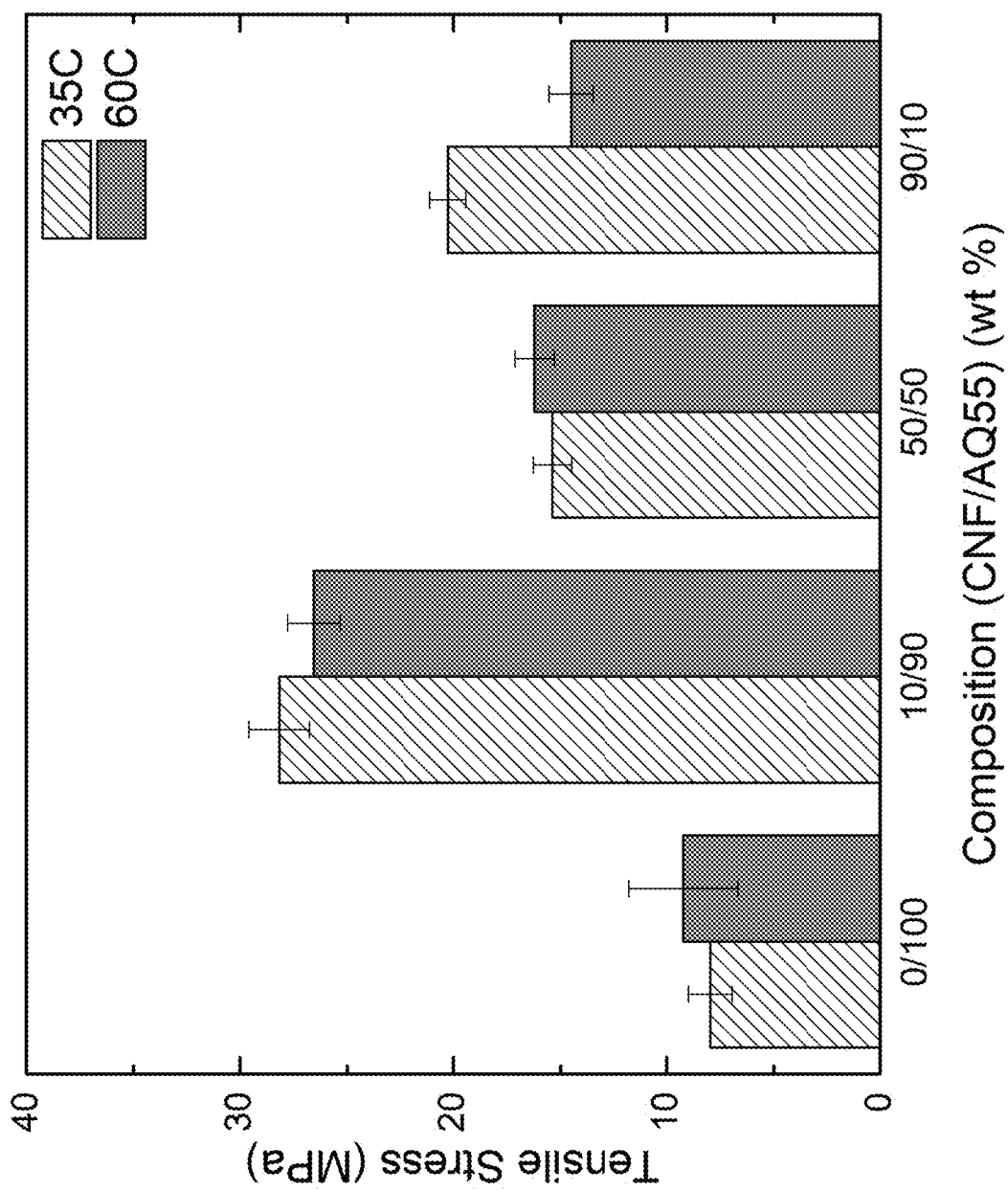
FIG. 9 shows experimental data for Tensile Strength for dried films made from suspensions having different polymer concentrations, where the films were dried at either 35° C. or 60° C.
Figure 10:
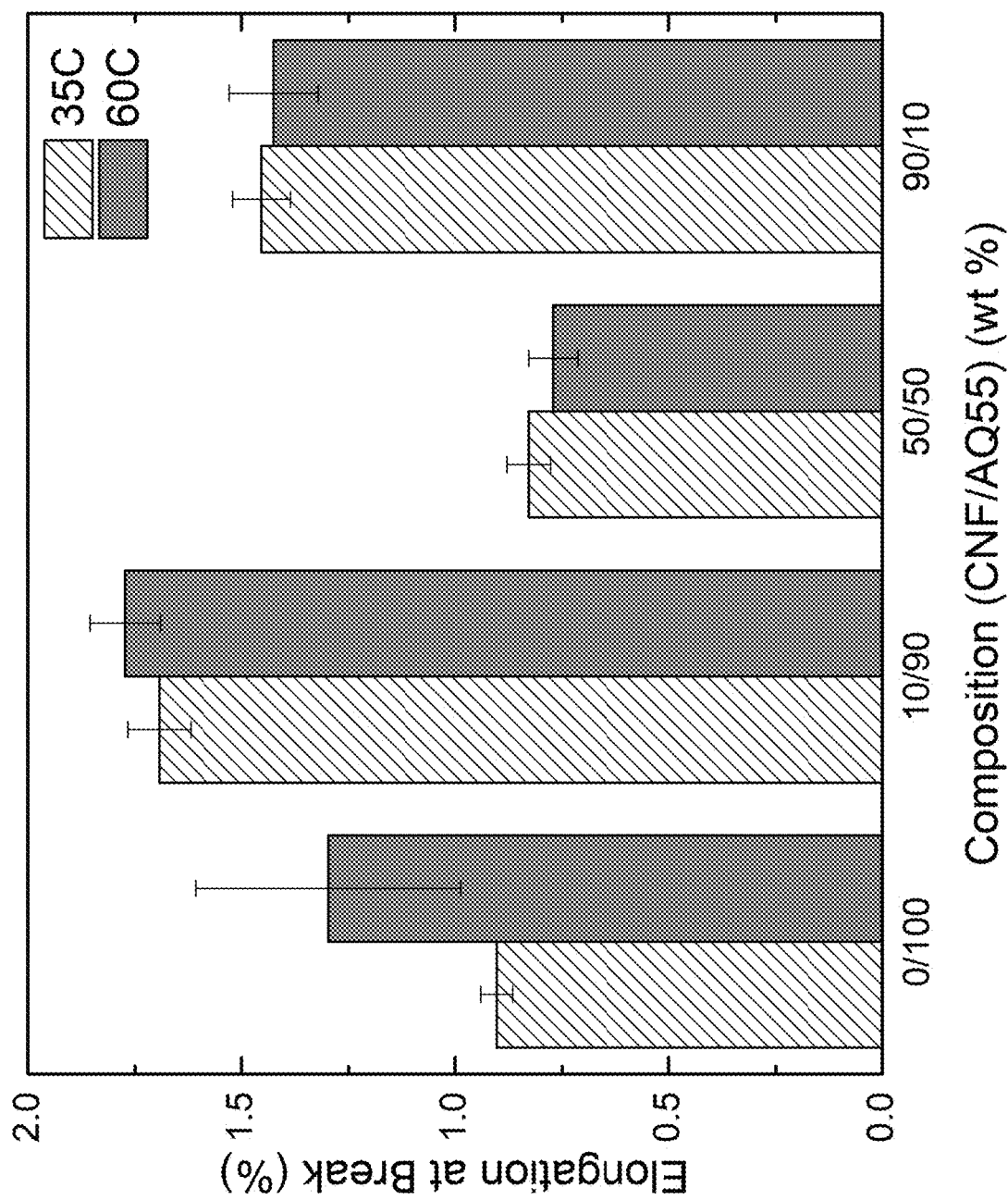
FIG. 10 shows experimental data for Elongation at Break for dried films made from suspensions having different polymer concentrations, where the films were dried at either 35° C. or 60° C.
Figure 11:
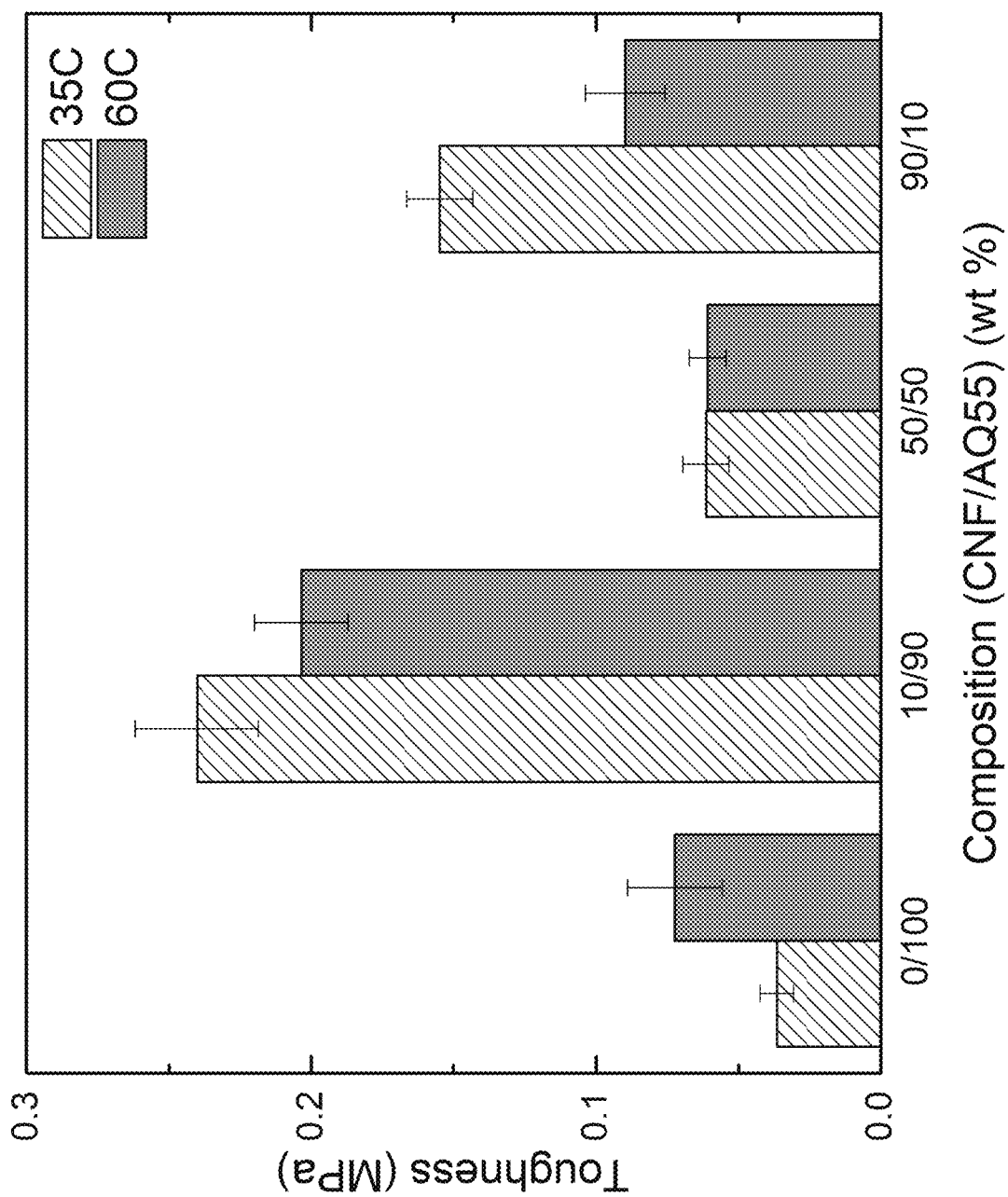
FIG. 11 shows experimental data for Toughness for dried films made from suspensions having different polymer concentrations, where the films were dried at either 35° C. or 60° C.

FIG. 3 shows the viscosity increase with respect to concentration at a selected shear rate of 10 $s^{-1}$. Mixtures with different sulfonated polyesters were tested: Eastman AQ™ 38, Eastman AQ™ 48, and Eastman AQ™ 55. A mixture with PVA and a mixture without any polymer were also tested. The viscosity increase is more dramatic for the mixture with PVA than the polyester-containing mixtures.

Based on the data, it appears that 2-8 wt % polyester imparts film formation-ability without substantially altering the mixture viscosity. If moderate viscosity alterations can be tolerated, 0.2-25 wt % polyester can be used.

B. Mechanical Property Experiments

In a set of experiments, various mixtures were prepared and tested to evaluate and compare bulk mechanical properties of composite films prepared under different conditions. For instance, different types of sulfonated polyesters were evaluated. Also tested was the ratio of cellulose nanofibril to polymer in prepared suspensions. Also tested was drying at temperatures below and above the glass transition temperature of sulfonated polyesters.

The same stock dispersions of Eastman AQ™ polymers and cellulose nanofibril as used to prepare test mixtures 1-9 above were used to prepare composite films for these tests. Calculated amounts of each component and deionized water were added into a beaker and stirred with a magnetic stir plate for an hour to ensure dispersion. The dispersion was then sonicated using the probe sonicator for desired energy input, with 60% amplitude and pulsing application of energy 2 seconds on, 3 seconds off. The dispersion was then poured into a 9 cm by 9 cm square polystyrene Petri dish and dried at a desired temperature (35° C. or 55° C.) in gravity convection oven for at least a week. Last, the films were dried under vacuum for 24 hours for complete removal of water. Table 2 below provides details of the tested films.

TABLE 2

Composition of samples tested for data shown in FIGS. 4-11.

| Type of sulfonated polyester | Composition (Cellulose nanofibril/Polyester) | Sample film thickness (μm) |
|---|---|---|
| AQ38 | 0/100 | 593 ± 37 |
|  | 5/95 | 407 ± 24 |
|  | 10/90 | 255 ± 8 |
|  | 20/80 | 192 ± 20 |
| AQ48 | 0/100 | 228 ± 12 |
|  | 5/95 | 400 ± 3 |
|  | 10/90 | 237 ± 18 |
|  | 20/80 | 142 ± 8 |

TABLE 2-continued

Composition of samples tested for data shown in FIGS. 4-11.

| Type of sulfonated polyester | Composition (Cellulose nanofibril/Polyester) | Sample film thickness (μm) |
|---|---|---|
| AQ55 | 0/100 | 258 ± 22 |
|  | 5/95 | 266 ± 26 |
|  | 10/90 | 234 ± 30 |
|  | 20/80 | 194 ± 26 |

The thickness of samples varied from 134 μm to 630 μm, depending on the composition of sulfonated polyesters and cellulose nanofibril as well as the degree of sulfonation of polyesters used. Samples were cut into strips of 6 cm×0.6 cm with a $CO_2$ laser on a Universal Laser VL3.50 system (Universal Laser Systems, Inc., Scottsdale, Arizona). Quasi-static uniaxial tensile tests were performed on Instron Universal Machine 5943 (Instron, Norwood, Massachusetts). The samples were strained at a speed of 1 mm/minute.

Data shown in FIGS. 4-11, namely, Young's modulus, tensile stress, elongation at break, and toughness of the composite film were extracted from tensile stress vs. strain curves. Young's modulus was measured by the slope at the elastic zone; tensile stress was the maximum stress before failure; elongation at break was calculated by finding the ratio between change in length and initial length $$\left(\frac{\Delta \text{length}}{\text{initial length}}\right);$$

and toughness was measured by calculating the area under the stress vs. strain curve.

FIGS. 4-7 show the change in mechanical properties (Young's modulus, tensile stress, elongation at break and toughness) of three different sulfonated polyesters and cellulose nanofibril composite films. For most cases, adding small amount of cellulose nanofibril (5 wt % cellulose nanofibril in solid) led to an improvement in all four criteria. However, further cellulose nanofibril addition led to a decrease in some of the properties due to inevitable cellulose nanofibril aggregation, allowing less interaction between cellulose nanofibril and polymer matrix.

FIGS. 8-11 show mechanical property data for composite films including AQ55 polyester, where two different drying temperatures and drying times were applied. Composite films were either dried at 35° C. for about 7 days or dried at 55° C. for about 3 days, where 35° C. is below the polymer's glass transition temperature and 55° C. is above the polymer's glass transition temperature. Based on data shown in FIGS. 8-11, drying temperature does not appear to have a significant effect on the strength of the composite films.

Figure 12:
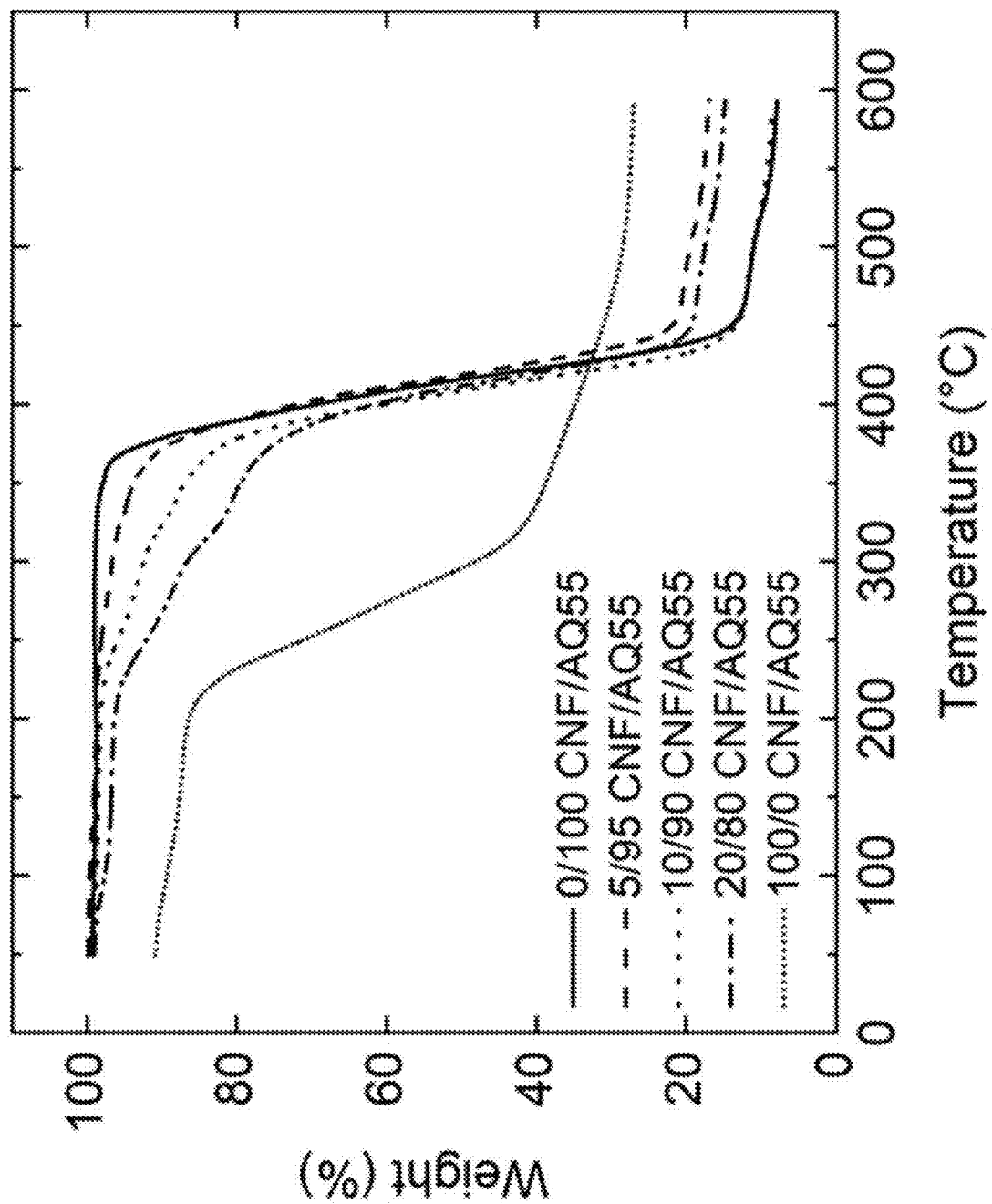
FIG. 12 shows thermal stability data for dried films made from suspensions having different ratios of polymer to cellulose nanofibril.

FIG. 12 shows thermal stability data for composite films with different ratios of polymer to cellulose nanofibril. The same stock dispersion of Eastman AQ™ 55 polymer and cellulose nanofibril as used to prepare test mixtures 1-9 above were used to prepare composite films for these tests. That is, calculated amounts of each component and deionized water were added into a beaker and stirred with a magnetic stir plate for an hour to ensure dispersion. The dispersion was then sonicated using the probe sonicator for desired energy input, with 60% amplitude and pulsing application of energy 2 seconds on, 3 seconds off. The dispersion was then poured into a 9 cm by 9 cm square polystyrene Petri dish and dried at a desired temperature (35° C. or 60° C.) in gravity convection oven for at least a week. Last, the films were dried under vacuum for 24 hours for complete removal of water. Table 3 below provides details of the tested films.

TABLE 3

Composite film components for data shown in FIG. 12.

| Type of sulfonated polyester | Composition (Cellulose nanofibril/Polyester) |
|---|---|
| AQ55 | 0/100 |
|  | 5/95 |
|  | 10/90 |
|  | 20/80 |
|  | 100/0 |

Thermal gravimetric analysis of the sample films in Table 3 was performed on SDT 650 Simultaneous Thermal Analyzer (TA Instruments, New Castle, Delaware). Samples of 10-20 mg were placed into an alumina pan and equilibrated at 50° C., followed by ramping at a rate of 10° C./min to 600° C. Samples were kept at elevated temperature isothermally for an hour before the samples were cooled back down to room temperature.

As shown in FIG. 12, pure cellulose nanofibril film showed the lowest thermal stability, whereas pure AQ55 film showed the highest thermal stability. The thermal stability performance of composite films fall between the pure cellulose nanofibril film and the pure AQ55 films. Adding a small amount of cellulose nanofibril (5 wt %) appears to have led to a slight reduction in thermal performance, and greater amounts of cellulose nanofibril appear to have led to a large drop in degradation temperature.

It is understood that the foregoing detailed description and accompanying examples are merely illustrative and are not to be taken as limitations upon the scope of the disclosure.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use, may be made without departing from the spirit and scope of the disclosure.

What is claimed is:

1. A suspension, comprising:
   a polar solvent;
   sulfonated polyester material dispersed in the polar solvent; and
   cellulose nanofibril material dispersed in the polar solvent;
   wherein the cellulose nanofibril material is present at no less than 3.0 wt % and at no more than 10 wt % of the suspension.

2. The suspension according to claim 1, wherein the cellulose nanofibril material is a carboxylated cellulose nanofibril.

3. The suspension according to claim 2, wherein the sulfonated polyester material is present at no less than 1.8 wt % of the suspension.

4. The suspension according to claim 2, wherein the sulfonated polyester material is present at no less than 12 wt % of the suspension.

5. The suspension according to claim 1, wherein the sulfonated polyester material is present at no more than 25 wt % of the suspension.

6. The suspension according to claim 1, wherein the polar solvent is an aqueous solvent.

7. The suspension according to claim 1, wherein the polar solvent is ethylene glycol.

8. The suspension according to claim 1, wherein the suspension is stable for at least 24 hours.

9. The suspension according to claim 1, wherein the suspension, after drying for at least 3 days at a temperature of at least 35° C. and no greater than 60° C. becomes a dried polymer film, the dried polymer film having a Young's Modulus of 1000 MPa to 2500 MPa.

10. The suspension according to claim 1, wherein the suspension, after drying for at least 3 days at a temperature of at least 35° C. and no greater than 60° C. becomes a dried polymer film, the dried polymer film having a tensile strength of 10 MPa to 30 MPa.

11. The suspension according to claim 1, wherein the suspension, after drying for at least 3 days at a temperature of at least 35° C. and no greater than 60° C. becomes a dried polymer film, the dried polymer film having a toughness of 0.1 MPa to 0.25 MPa.

12. A method for making an aqueous suspension, the method comprising:
   combining an aqueous sulfonated polyester dispersion and an aqueous cellulose nanofibril dispersion to form the aqueous suspension;
   wherein cellulose nanofibril material is present at no less than 3.0 wt % and at no more than 10 wt % of the aqueous suspension.

13. The method according to claim 12, further comprising mixing the combined aqueous sulfonated polyester dispersion and aqueous cellulose nanofibril dispersion.

14. The method according to claim 13, further comprising drying the combined aqueous sulfonated polyester dispersion and aqueous cellulose nanofibril dispersion, thereby generating a dried polymer film.

15. The method according to claim 14, wherein drying occurs at a drying temperature no less than 35° C. and no greater than 60° C.

16. The method according to claim 14, wherein the drying temperature is no less than 55° C.

17. The method according to claim 14, wherein the dried polymer film has a Young's Modulus of at least 1250 MPa.

18. The method according to claim 13, wherein mixing includes probe sonication in an ice bath.

* * * * *

UNITED STATES PATENT AND TRADEMARK OFFICE
CERTIFICATE OF CORRECTION

PATENT NO. : 12,421,663 B2
APPLICATION NO. : 17/609107
DATED : September 23, 2025
INVENTOR(S) : Emily Facchine et al.

Page 1 of 1

It is certified that error appears in the above-identified patent and that said Letters Patent is hereby corrected as shown below:

In the Claims

Claim 3, Column 12, Line 1: please replace "claim 2" with --claim 1--

Claim 3, Column 12, Line 2: please replace "less than 1.8 wt %" with --more than 25 wt %--

Claim 4, Column 12, Line 5: please replace "12 wt %" with --1.8 wt %--

Claim 5, Column 12, Line 7: please replace "claim 1" with --claim 2--

Claim 5, Column 12, Line 8: please replace "more than 25 wt %" with --less than 12 wt %--

Signed and Sealed this
Eleventh Day of November, 2025

John A. Squires
*Director of the United States Patent and Trademark Office*